United States Patent

Grimm et al.

[11] 4,230,469
[45] Oct. 28, 1980

[54] DISTILLATION OF METHANE FROM A METHANE-CONTAINING CRUDE GAS

[75] Inventors: Peter Grimm, Pullach; Peter Burr, Munich, both of Fed. Rep. of Germany

[73] Assignee: Linde Aktiengesellschaft, Wiesbaden, Fed. Rep. of Germany

[21] Appl. No.: 917,752

[22] Filed: Jun. 21, 1978

[30] Foreign Application Priority Data

Jul. 28, 1977 [DE] Fed. Rep. of Germany ....... 2734080

[51] Int. Cl.² .................................................. F25J 3/02
[52] U.S. Cl. .......................................... 62/28; 62/40; 62/31
[58] Field of Search ........................... 62/28, 40, 24, 31

[56] References Cited

U.S. PATENT DOCUMENTS

| | | | |
|---|---|---|---|
| 2,713,781 | 7/1955 | Williams | 62/40 |
| 2,823,523 | 2/1958 | Eakin et al. | 62/40 |
| 3,509,728 | 5/1970 | Mercer et al. | 62/28 |

Primary Examiner—Norman Yudkoff
Attorney, Agent, or Firm—Millen & White

[57] ABSTRACT

In the separation in a rectification column of methane and optionally lower-boiling components from a methane-containing crude gas, which gas contains additionally higher-boiling hydrocarbons, hydrogen sulfide, carbon dioxide, or mixtures thereof, wherein an auxiliary cycle containing a fluid medium is employed for the production of cooling to produce reflux liquid at the head of the rectifying column, an improvement is provided wherein liquid in the rectifying column positioned above the column sump and below the column head, is vaporized in indirect heat exchange with condensing cycle medium.

6 Claims, 1 Drawing Figure

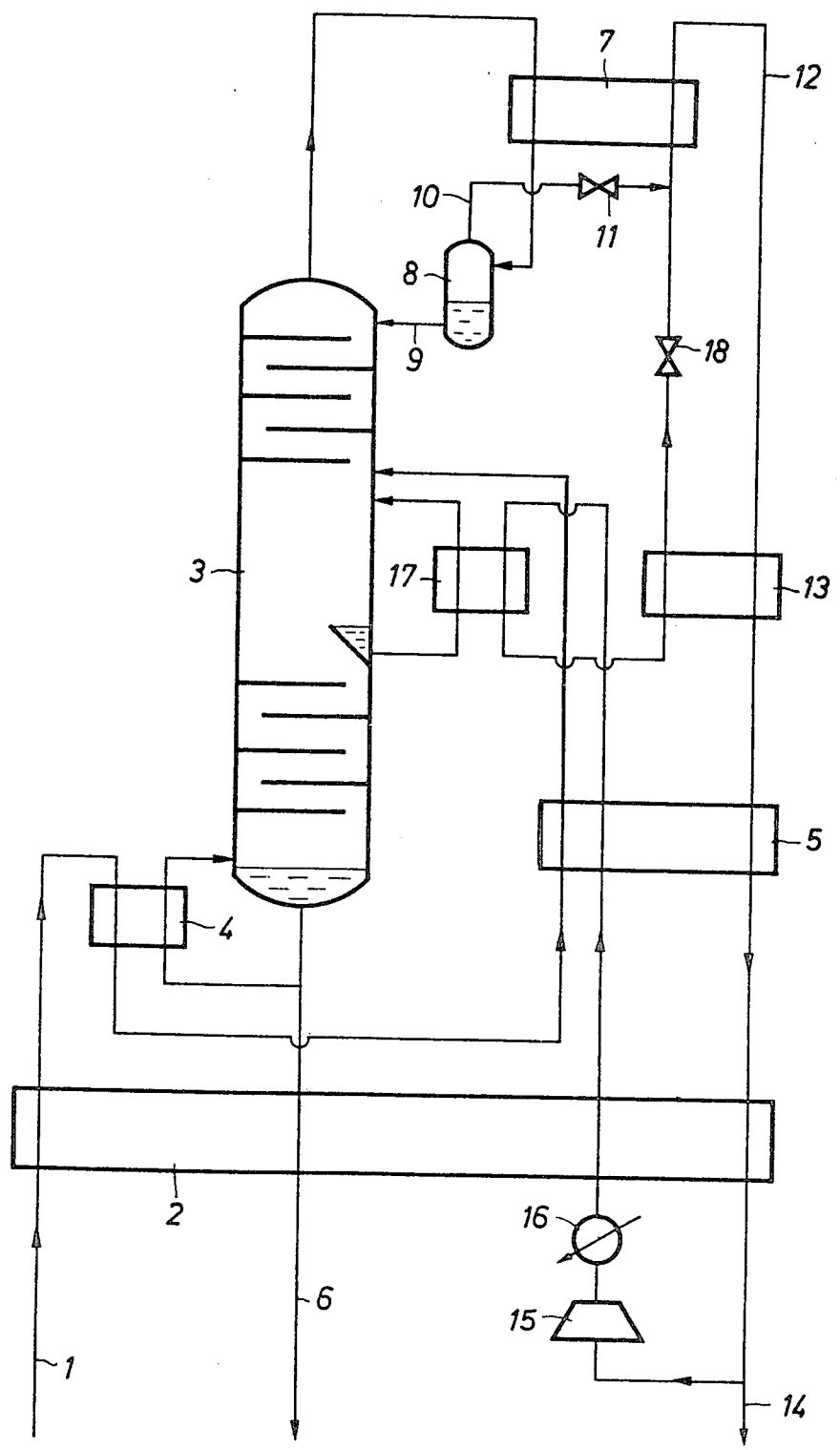

DISTILLATION OF METHANE FROM A METHANE-CONTAINING CRUDE GAS

BACKGROUND OF THE INVENTION

This invention relates to the distillation of methane and optionally lower-boiling components from a methane-containing crude gas, e.g., natural gas.

Such a method is described in DAS [German Published Application] No. 1,619,728 in two variations, the contents of said DAS being incorporated by reference herein. Both cases involve the separation of a methane-ethylene mixture.

The first of these conventional processes resides in using a single auxiliary cycle for condensing overhead vapor to provide reflux liquid at the head of the column and for providing heat to produce reboiler vapor in the column sump; the medium of this auxiliary cycle contains methane. However, this process has the disadvantage that the column pressure can not be more than 3 bar, and the pressure difference to be provided by the cycle compressor must be at least 30 bar. The compression ratio required in the auxiliary cycle is thus at least 11.

In the second conventional process variation, a mixture cycle is utilized for cooling the head of the column to provide reflux liquid and for heating the column sump to provide vapor; the medium of this mixture cycle contains at least two components, expecially methane and ethylene. The cycle is subdivided into two branches after the partial condensation of the cycle medium resulting from the heating of the column sump. Thereafter only the lower-boiling component is used, after throttle expansion, for the cooling of the column head. The permissible column pressures according to this mode of operation range between 2.5 and 5 atmospheres absolute. The cycle medium must be compressed to maximally 18 atm. abs., there being the prerequisite that the cycle pressure during heat exchange with the head product of the column is to be lower than the column pressure, since the heat exchanging media of the head cooling on both sides involve greatly enriched methane. The compression ratio to be produced by the cycle compressor is, in this case, at least about 4, and in the mode of operation disclosed in DAS No. 1,619,728 even 15-18.

The disadvantages of the two conventional variations of the process reside, accordingly, in the relatively low column pressures involved and the relatively high compression ratios required in the auxiliary cycle. As a consequence, there is the necessity of providing large dimensions for the column and of incurring a high operating energy consumption when conducting the process.

SUMMARY OF THE INVENTION

An object of the present invention resides in providing an improved process of the type mentioned above, and especially improved with respect to energy utilization and the variability in the selection of the process pressure.

Upon further study of the specification and appended claims, further objects and advantages of this invention will become apparent to those skilled in the art.

To attain these objects, there is provided in the separation in a rectification column of methane and optionally lower-boiling components from a methane-containing crude gas, which gas contains additionally higher-boiling hydrocarbons, hydrogen sulfide, carbon dioxide, or mixtures thereof, wherein an auxiliary cycle containing a fluid medium is employed for the production of cooling to produce reflux liquid at the head of the rectifying column, the improvement wherein liquid in the rectifying column positioned above the column sump and below the column head is vaporized in indirect heat exchange with condensing cycle medium.

BRIEF DESCRIPTION OF THE DRAWING

Various other objects, features and attendant advantages of the present invention will be more fully appreciated as the same becomes better understood when considered in conjunction with the accompanying drawing, in which like reference characters designate the same or similar parts throughout the several views, and wherein the figure shows schematically an embodiment of the process of this invention using an open auxiliary cycle and sump heating effected by crude gas.

DETAILED DISCUSSION

The advantages attainable by the invention as compared with the conventional process variations reside, on the one hand, in making far higher operating pressures feasible in the rectifying column, e.g., 20 to 40 bar, preferably 34 to 38 bar, and, on the other hand, in providing the possibility of reducing the compression ratio in the auxiliary cycle. Typical such ratios are 2 to 4, preferably 2 to 3. The last-mentioned advantage is due to the fact that the temperatures governing the selection of the pressure difference in the auxiliary cycle are no longer dependent on the temperature difference between the sump of the column and the head of the column. Consequently, the compression ratio is no longer dependent, to the same extent as in conventional processes, on the requirements derived from considerations of product purity. In the process of this invention, the heat to be emitted by the compressed cycle medium is exchanged at a lower temperature level. As a result, more liquid is produced during the subsequent isenthalpic throttling step, and the expanded cycle medium can absorb a greater amount of heat during the head cooling step. Simultaneously, this means that the purity of the product to be withdrawn from the head of the rectifying column can be increased inasmuch as the amount of the reflux liquid product is enlarged.

The basic features of the methane distillation process are well known and are described, for example, in DAS No. 1,619,728 and whose disclosure is incorporated by reference herein with regard to all process parameters not otherwise discussed herein.

The location in the rectification column at which the inventive vaporization of liquid is to be effected is not critical as long as it is at about the middle of the column. Generally, in a column having x theoretical plates, the liquid to be vaporized should be subjected to the heat exchanging of this invention in the region of theoretical plates numbers $0.4x$–$0.6x$. Correspondingly, for a column having y actual plates, the vaporization should be carried out in the region of plates numbers $0.4y$–$0.6y$. For example, in columns having a relatively small number of total actual plates, e.g. of the type bubble cap plates, such as 5–10, the liquid should be vaporized in the region of plates 2–6; for larger numbers of total actual plates, e.g. 50–60, the liquid should be vaporized in the region of plates 20–36. In typical columns, the liquid in these regions is at a temperature of 175°–205°

K.; corresponding to a pressure of 20–40 bar. Typically, of the total amount of liquid present in this vaporization region, from 20–80 weight percent is vaporized, the remainder cascading downward in conventional fashion.

The temperature of the cycle medium at the point where it is used to vaporize the reflux liquid is usually 180°–215° K.

The need for sump heating, which still exists in spite of the vaporization of the liquid fraction per this invention approximately in the center of the column, is suitably satisfied by heating the column sump with crude gas and/or cycle medium.

As can be seen from the example below, since the process of this invention can be conducted at far higher pressures than those used in conventional process variations, it is possible to process natural gas, which may be under pressure, in an advantageous fashion and to discharge and store the thus-produced pure methane likewise under pressure.

Since a high purity product methane can be produced by the process of this invention, an open auxiliary cycle can be used with advantage. In this mode of operation, as illustrated in the example below, gaseous product methane is expanded and combined with the likewise expanded cycle medium. These are used together for producing the reflux liquid at the head of the column, some of the mixture being branched off as product gas from this cycle medium prior to compression. The use of such an open cycle has the advantage that the unavoidable leakage losses can be directly compensated for by the product methane fed thereto.

However, it may also be advantageous to utilize a closed auxiliary cycle wherein a mixture of ethane and/or ethylene and/or higher-boiling hydrocarbons circulates as the cycle medium. This mode of operation affords the advantage that an even better adaptation to the unprecedentally optimum conditions in the rectifying column is made possible by such a varying composition, as well as by the resultant differing boiling points of the cycle medium.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following example, all temperatures are set forth uncorrected in degrees Celsius; unless otherwise indicated, all parts and percentages are by weight.

EXAMPLE

Through a conduit 1, 19,100 Nm$^3$/h. of crude gas is introduced. The crude gas contains, in addition to methane, 14.5 mol-% of nitrogen, 0.9 mol-% of carbon dioxide, as well as 2.9 mol-% of ethane and higher-boiling hydrocarbons. It is under a pressure of 38 bar. In a heat exchanger 2, the crude gas is cooled against sump liquid and against product gas from a rectifying column 3 to a temperature of 239° K. The crude gas is then utilized in a heat exchanger 4 for heating the column sump and thereafter reaches a temperature of 212° K. This crude gas is further cooled against cold product gas in a heat exchanger 5 to 192° K. and thereafter introduced into the rectifying column 3.

The rectification takes place under a pressure of 36 bar. A portion of the sump liquid is vaporized in heat exchanger 4 and reintroduced into the column. Finally, via conduit 6, 1,550 Nm$^3$/h. of a sump product is discharged which contains, in addition to methane, 35.8 mol-% of ethane, 10.1 mol-% of carbon dioxide, as well as 0.05 mol-% of nitrogen. At a temperature of 177° K., 39,200 Nm$^3$/h. of a gas is withdrawn from the head of the rectifying column which contains, in addition to methane, 10.6 mol-% of nitrogen, 0.2 mol-% of carbon dioxide, and 0.01 mol-% of ethane, as well as higher-boiling hydrocarbons. The larger part of this gas is liquefied in a heat exchanger 7 and subjected to phase separation in a separator 8. The thus-liquefied proportion of 21,650 Nm$^3$/h. is recycled into the column as reflux liquid via conduit 9. The proportion of 17,550 Nm$^3$/h. which remains in the gaseous phase is withdrawn from the head of separator 8 via conduit 10 and expanded in an expansion valve 11 to a pressure of 21 bar. The phase separation in separator 8 takes place at a temperature of 175° K.

The product gas expanded in expansion valve 11 is fed into conduit 12 of an auxiliary cycle, warmed in heat exchangers 13, 5, and 2, and withdrawn via conduit 14. The product gas contains, in addition to methane, 15.77 mol-% of nitrogen, 0.09 mol-% of carbon dioxide, and 0.01 mol-% of ethane and higher-boiling hydrocarbons.

The cycle medium circulated in the auxiliary cycle has the same composition as the product gas. The circulated amount of the cycle medium, compressed to 50 bar in compressor 15, is 22,350 Nm$^3$/h. After removal of the compression heat by means of external cooling in a cooler 16, the cycle medium is cooled in heat exchangers 2 and 5 to 216° K. and 195° K., respectively. Thereafter, the cycle medium passes into the heat exchanger 17 where it is partially liquefied against evaporating liquid from the rectifying column. The liquid from the rectifying column has a temperature of 187° K. upon entering the heat exchanger 17, whereas the partially liquefied cycle medium exiting from the heat exchanger has a temperature of 190° K. After further cooling in heat exchanger 13 to 186° K., as well as expansion to 21 bar in the expansion valve 18, the cycle medium is mixed at a temperature of 166° K. with the product gas discharged from expansion valve 11. Both gas portions are then utilized for producing the reflux liquid in heat exchanger 7 and further conveyed together through conduit 12.

The preceding example can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a separation in a rectification column of methane and optionally lower-boiling components from a methane-containing crude gas, which gas contains additionally higher-boiling hydrocarbons, hydrogen sulfide, carbon dioxide, or mixtures thereof, wherein an auxiliary cycle containing a fluid medium is employed for the production of cooling to produce reflux liquid at the head of the rectifying column, the improvement wherein liquid in the rectifying column located in the region of plates numbers 0.4 x–0.6 x, wherein x is the number of theoretical plates in the column, is vaporized in indirect heat exchange with condensing auxiliary cycle medium, without said condensing auxiliary cycle medium reboiling the bottoms, and reboiling the bottoms with feed to the rectification column without indirect heat exchange in said region of plates.

2. The process of claim 1, wherein an open auxiliary cycle is utilized wherein gaseous product methane is expanded and combined with the auxiliary cycle medium which has been expanded after passage through the liquid vaporization operation; the mixture of the two sources of methane being used as heat exchange medium to produce the reflux liquid at the column head, and subsequently being divided into two flows, one forming the product gas and the other subsequently being compressed and used as a heat exchange medium to vaporize the reflux liquid.

3. The process of claim 1, wherein a closed auxiliary cycle is utilized wherein a mixture of ethane, ethylene or higher-boiling hydrocarbons circulates as the auxiliary cycle medium.

4. The process of claim 1, wherein the temperature of the reflux-liquid in the region of the column in which it is vaporized by the condensing auxiliary cycle medium is 175°–205° K. and the temperature of the condensing auxiliary cycle medium used to effect the vaporization is 180°–275° K.

5. The process of claim 1, wherein the liquid which is vaporized in heat exchange with condensing auxiliary cycle medium is located at about the middle of the column.

6. In the separation in a rectification column of methane and optionally lower-boiling components from a methane-containing crude gas, which gas contains additionally higher-boiling hydrocarbons, hydrogen sulfide, carbon dioxide, or mixtures thereof, wherein an auxiliary cycle containing a fluid medium is employed for the production of cooling to produce reflux liquid at the head of the rectifying column located in the region of plates numbers $0.4\,x$–$0.6\,x$, wherein x is the number of theoretical plates in the column, is vaporized in indirect heat exchange with condensing auxiliary cycle medium, wherein an open auxiliary cycle is utilized wherein gaseous product methane is expanded and combined with the auxiliary cycle medium which has been expanded after passage through the liquid vaporization operation; the mixture of the two sources of methane being used as heat exchange medium to produce the reflux liquid at the column head, and subsequently being divided into two flows, one forming the product gas and the other subsequently being compressed and used as a heat exchange medium to vaporize the reflux liquid.

* * * * *